(12) United States Patent
Hoenes et al.

(10) Patent No.: US 8,603,394 B2
(45) Date of Patent: Dec. 10, 2013

(54) MEASUREMENT SYSTEM WITH DISTRIBUTED FUNCTIONS

(75) Inventors: Joachim Hoenes, Zwingenberg (DE); Bruno Thoes, Quierschied (DE); Joerg Scherer, Aalen (DE); Karl Werner, Wiesloch (DE); Volker Zimmer, Laumersheim (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 279 days.

(21) Appl. No.: 12/114,266

(22) Filed: May 2, 2008

(65) Prior Publication Data

US 2009/0022630 A1     Jan. 22, 2009

(30) Foreign Application Priority Data

May 4, 2007   (EP) ..................................... 07107520

(51) Int. Cl.
 *G01N 15/06*   (2006.01)
(52) U.S. Cl.
 USPC ........... 422/68.1; 422/82.05; 422/52; 422/73; 422/82.01; 422/82.06; 250/214.1; 250/251; 436/43
(58) Field of Classification Search
 None
 See application file for complete search history.

(56) References Cited

U.S. PATENT DOCUMENTS

| 2004/0049355 A1* | 3/2004 | Maus et al. ..................... 702/19 |
| 2006/0094986 A1* | 5/2006 | Neel et al. ..................... 600/583 |
| 2006/0222567 A1* | 10/2006 | Kloepfer et al. ............. 422/68.1 |

FOREIGN PATENT DOCUMENTS

| EP | 1702565 A2 | 9/2006 |
| EP | 1729128 A1 | 12/2006 |
| EP | 1764030 A1 | 3/2007 |
| WO | 2004/047642 A1 | 7/2004 |
| WO | 2004/056269 A1 | 7/2004 |
| WO | 2005/006985 A2 | 1/2005 |
| WO | 2006/002432 A1 | 1/2006 |
| WO | 2006/026741 A1 | 3/2006 |

* cited by examiner

*Primary Examiner* — Sally Merkling
(74) *Attorney, Agent, or Firm* — Krieg DeVault LLP

(57) ABSTRACT

An analysis system is provided which comprises an integrated analysis device and a test strip magazine, for determining an analyte in a body fluid, wherein the analysis system comprises a first group comprising reusable components and a second group of components comprising a plurality of disposable articles. The second group includes non-electronic and electronic components, with critical interfaces configured between two or more such components, wherein non-electronic components can be disconnected from electronic components at a disconnection point. In one embodiment, critical interfaces are produced and tested during production of the analysis system.

17 Claims, 3 Drawing Sheets

MEASUREMENT SYSTEM WITH DISTRIBUTED FUNCTIONS

CLAIM OF PRIORITY

The present application is based on and claims priority to European Patent Application No. 07 107 520.4, filed May 4, 2007, which is hereby incorporated by reference in its entirety.

TECHNICAL FIELD OF THE INVENTION

The present application relates to an analysis system for determining an analyte in a body fluid, and more particularly to an integrated analysis system comprising an analysis device and a test strip magazine having simplified coupling therebetween.

BACKGROUND

Integrated systems for blood glucose measurement have been available commercially for some time. These integrated systems typically comprise a measurement device, a battery which can be inserted in it, and a test strip magazine. The test strip magazine may be in the form of a disc (e.g., Bayer® Dex) or may be configured in the form of a drum (e.g., ACCU-CHEK® Compact). Other forms for test strip magazines are also known in the art. Test strip magazines generally contain some kind of simple, built-in coding means, for example in the form of a barcode for transferring batch-specific information to the measurement device on which the test strip magazine is used. For cost reasons, the information content contained in the more simple coding means is limited. For most integrated analysis systems, more complex electronic coding means, such as ROM keys, which contain a much larger amount of information and thus are intrinsically correspondingly more flexible, are not used.

Coding means such as ROM keys which have a high information content are intended to be used in more recent developments. This therefore results in the problem on the one hand of reducing the costs but on the other hand of solving the problem of the remaining electronics scrap in conjunction with the domestic refuse problem.

Reliable coupling of any type of coding means to the measurement device represents one critical interface for an analysis system. Electrical contacts for a ROM key or a smart card require compliance with tight mechanical tolerances and the use of contacts which can be reused many times. Although RFID chips can be read without contact, they lead, in the final analysis, to higher costs, however, and to considerably greater energy consumption.

Examples of integrated systems are known in the prior art, including PCT Publication Nos. WO 2005/006985, WO 2004/047642, WO 2004/056269, and WO 2006/002432, the disclosures of which are hereby incorporated herein by reference in their entireties. As can be understood from these publications, test element magazines can include a tape or ribbon of test elements, and other integrated systems additionally include a piercing member for obtaining a body fluid such as blood by piercing a body part. Also, prior art systems describe different means for sealing a test element magazine to protect test elements from exposure to the environment and other fouling factors. In many prior art systems, the integration focuses primarily on the magazine holding the test elements.

The development trends for analysis devices which can be handled by the user are heading towards future containers for test elements being in the form of ribbon or tape cassettes. The test media are held in the cassettes as a ribbon or tape which, for example, is provided in places with a single-layer or multiple-layer coating for analyte determination. Furthermore, these cassettes contain mechanical elements for transport of the test elements, which can be viewed as test strips provided in ribbon form, as well as keys, in particular for the outlet opening of the unused ribbon material from a supply chamber within the magazine. In most instances, the tape cassette configuration solutions require the magazine to be inserted into the analysis device thus leading to the analysis device itself being physically relatively large. For other magazine configuration solutions known in the art, such as magazines or dispensers carrying test element strips in a stacked orientation, such insertion is not required, but rather the magazine may be mounted or otherwise placed into contact with the measurement device to feed test strips, and a system of mechanisms, housings and moveable seals are configured for positioning test strips for analysis while maintaining an essentially moisture-tight and essentially air-tight magazine package.

In virtually all the devices which are known from the prior art, the critical interface between the disposable (which should be understood as meaning test strips and the test strip magazine) and the measurement device is produced or otherwise caused by the customer. Moreover, the physical complexity and the costs for the interface are considerable without being able to ensure effective functional reliability in all cases.

SUMMARY

An object of the present invention is to simplify the coupling between an analysis device and a test element magazine, designing it to be more reliable, avoiding electronics scrap, and saving costs by reuse. This object and others that will be apparent from this disclosure to those of ordinary skill in the art are achieved by various embodiments of the present invention.

According to one embodiment, the present invention provides a measurement unit for evaluation of test elements which have been wetted with a body fluid. For example, as shown in FIGS. 4-5, the measurement unit 400 is integrated in a magazine 134 in which the test element material is stored in the form of a ribbon (which may also be described as a tape). The measurement unit 400 comprises a measurement peripheral 112 and measurement electronics 110 (FIG. 3) such as, for example, optics associated with electronics with LEDs, photodiodes and at least one circuit board, such as an ASIC. The at least one ASIC typically contains a serial interface 406 which, for example, can be fitted to a rear face 404 of the housing 402 of the magazine 134, so that the analysis device 420 can simply be plugged onto the serial interface 406 in order to emit preprocessed data which is present at the serial interface, for example relating to a glucose measurement. Embodiments of the magazine 134 proposed according to the present invention for holding the test strip material which is in the form of a ribbon allows the magazine 134 to be mechanically coupled to the analysis device 420 more easily. It also has a greater level of integration. Furthermore, signals are transmitted robustly via the serial interface 406, which may be provided either on the rear face 404 of the housing 402 of the magazine 134 or one of its side surfaces, by means of a serial protocol between the magazine 134, which has a higher level of integration, and the analysis device 420 which can easily be connected thereto. This creates the basis for smaller physical forms both for the analysis device 420 and for the magazine 134, which is in form of a cassette. Because of the fact that the more highly integrated magazine 134 proposed according to the invention need no longer be inserted or pushed into the analysis device 420, but can simply be plugged onto it, this results in greater design freedom for the physical size of the system.

The embodiments of the solution proposed according to the invention also permits moisture within the chamber of the magazine, in which the unused test strip supply is stored on a wound coil, to be measured by means of moisture sensors, as a result of the electronics being integrated in the cassette. Moisture ingress adversely affects the long-term use of the test strip material. The embodiments proposed according to the invention allow the moisture, which is either contained in this test strip material as a result of the production process or has entered it via an opening during use or while the test material is being fed out of the supply chamber, to be determined, thus allowing prediction of the remaining useful life of the test strip material stored in the supply chamber. The more highly integrated magazine proposed according to the invention is therefore able to provide the user with information about the quality and about the useful life which may remain for the unused test material supply.

The magazine which holds the test material which is in the form of a ribbon as proposed according to the embodiments of the present invention may also comprise a board which can be detachably connected to the magazine holding the test strip material, on which board at least one energy store is also accommodated. When the board is fitted to the housing of the magazine, for example by means of guide rails, or a bayonet fitting, for example by pushing it on, an electrical connection is made between the energy store arranged on the board and the electronics, for example, the ASIC, within the housing of the more highly integrated magazine. A ROM key for coding may also be arranged on the board. On the basis of the proposed embodiments, the board together with ROM key and energy store can be disconnected from the cassette, which holds the test strip material that is in the form of a ribbon, before disposal. While the contaminated test strip material can be disposed of in the domestic refuse, the board can either be disposed of during the course of electronics component disposal, or the user can collect each of the old boards and recycle them. The test strip material which can no longer be reused is disconnected, and the components which can be recycled, for example the board, can be fed back into the material cycle, and can be reused.

The present invention is to be explained in more detail by the following figures and examples.

BRIEF DESCRIPTION OF THE DRAWINGS

The following detailed description of the embodiments of the present invention can be best understood when read in conjunction with the following drawings, where like structure is indicated with like reference numerals and in which.

In order that the present invention may be more readily understood, reference is made to the following detailed descriptions and examples, which are intended to illustrate the present invention, but not limit the scope thereof.

DETAILED DESCRIPTION OF EMBODIMENTS OF THE PRESENT INVENTION

The following descriptions of the embodiments are merely exemplary in nature and are in no way intended to limit the present invention or its application or uses.

In the following text, the term 'magazine' means, generally, a holding element in which a number of test elements are held. The magazine may be in the form of a cassette, in which case the supply of test elements can be presented, for example in form of wound coils with one coil for unused test elements and one coil for used test elements. The magazine may also be in the form of a stack, in which case individual test elements can, for example, be held in strip form arranged vertically, horizontally or at an angle to one another. The magazine may also be in the form of a disc-type body on whose circumference individual test elements are held in slots, with a drive moving the magazine configured in the form of a disc on from one test element to another.

The present invention will be described in the following text with reference to a device having a test element supply in the form of ribbon strips, and with an optical evaluation capability; it should be noted, however, that the invention is not intended to be restricted to an embodiment such as this. The invention can be implemented just as well for a test element which can be evaluated electrochemically and is in the form of an individual test strip, and/or which is held in a stack magazine or some other embodiment.

In the following text, test elements should be understood as meaning a medical consumable material which, for example, is stored in strip form in the magazine and is used to determine an analyte in a human body fluid, for example blood glucose, lactate or cholesterol and the like. The term 'opening' in the following text should be understood as generally meaning an outlet opening for the medical consumable material which, for example, is in the form of test strips, from the magazine, and which for example may be in the form of a seal fitted to the housing of the magazine or a longitudinal slot with sealing lips in order to prevent undesirable ingress of moisture in the interior of the magazine holding the test elements.

Figure 1:
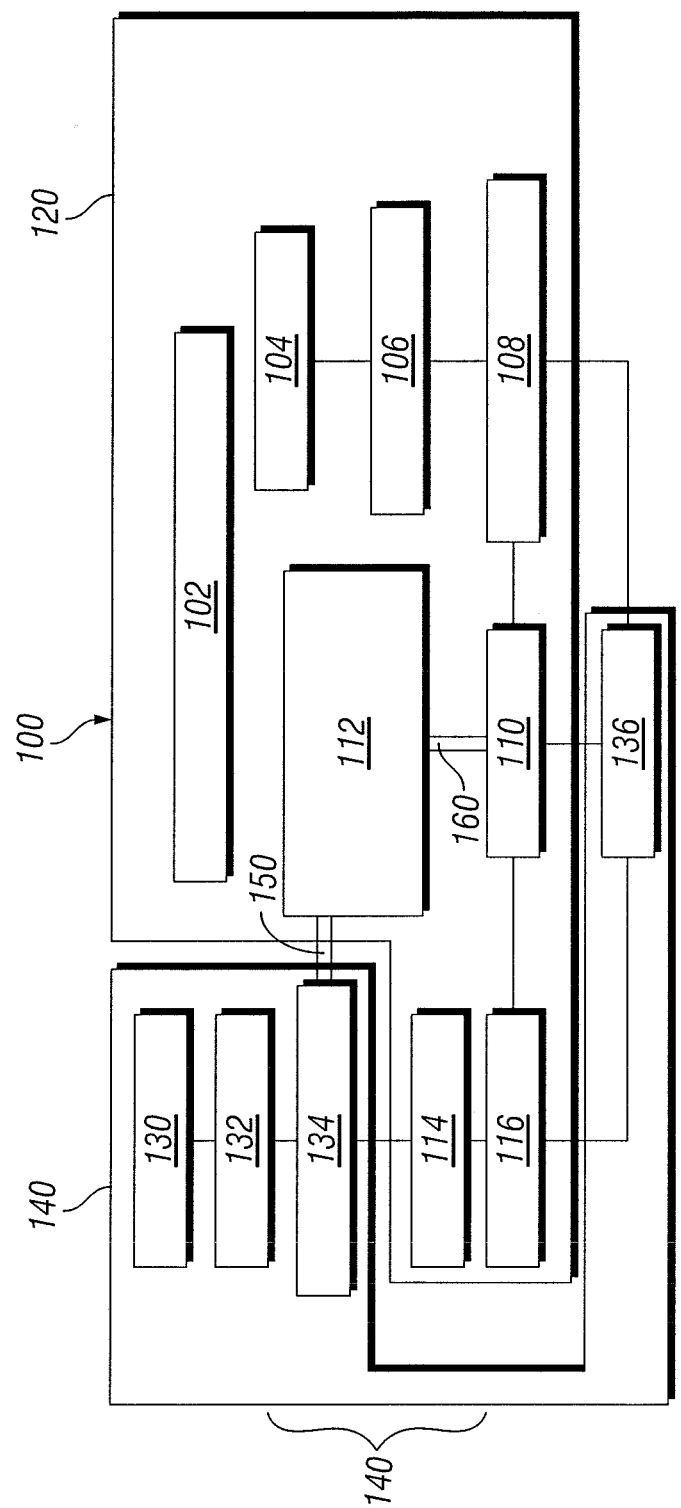
FIG. 1 illustrates a block diagram configuration of a device known from the prior art in which the elements of the device are combined in one group, and the elements of a disposable article are combined in another group.

The illustration in FIG. 1 shows a block diagram of the components of an analysis device known from the prior art. By way of example, this analysis device may be understood in the context of the ACCU-CHEK® Compact system produced by the applicant. The device 100, of which the major components are shown in FIG. 1, has a device housing 102 which is generally in the form of a plastic injection-moulded part. There is a display 104 in the device housing 102, on which the user can read the results obtained, for example, of the blood glucose content, cholesterol content and much more. The display 104 is integrated in the device housing 102 and is controlled via a display controller 106. The display controller 106 is itself connected to calculation electronics, which are annotated with the reference symbol 108 and in which the data displayed on the display 104 is calculated. The calculation electronics 108 in the device housing 102 are themselves in turn connected to measurement electronics 110, which are likewise accommodated in the device housing 102. A first critical interface 150 connects the disposable (that is to say the disposable part of the system) and the measurement device to one another. The first critical interface must be reproduced by the customer whenever each unused disposable is newly inserted, thus requiring correspondingly tight tolerances and therefore increased production costs.

The measurement electronics 110 are connected to a measurement peripheral 112 via a second critical interface 160. By way of example, the measurement peripheral of the device housing 102 of the device 100 as illustrated in FIG. 1 contains an optical evaluation system as well as other electronic components, for example a potentiometer and an ammeter for determining the current level. The electrical components which are integrated within the measurement peripheral 112 in the device housing 102 (the above list does not include all of these components) are used to evaluate a test strip which has been stored in a test strip magazine 134 and has been wetted with a body fluid such as blood, for example, by means of an opening which has previously been produced in the human skin, which body fluid is then examined for at least one analyte, using a chemical or optical process.

Furthermore, the device housing 102 contains a drive 114 which is used, for example, to feed test strips from the test strip magazine 134. The drive 114, which is generally an electrical drive has an associated drive controller 116.

As can be seen from the illustration in FIG. 1, the components mentioned above comprise a first group 120. That is, the device housing 102, the display 104, its display controller 106, the calculation electronics 108, the measurement electronics 110, the measurement peripheral 112 together with its components (including optics, ammeter, potentiometer etc.), the drive 114 and the drive controller 116 all form the collective elements of the device 100, and are combined in a group 120 in the illustration shown in FIG. 1.

The illustration in FIG. 1 also shows that a coding means 130 and a waste container 132 which is used to hold used test strips from the test strip magazine 134 represent components of a disposable article, which is annotated generally as a further group identified with the reference symbol 140 in the illustration in FIG. 1. An energy store 136 represents a further and separate energy store from the device 100. In this case, as in the case of many other devices in daily use, the battery contacts which make contact with the energy stores, typically in the form of batteries, represent a source of frequent malfunctions.

In the prior art solution illustrated in FIG. 1, the first interface 150 is located between the group 140 of components of the disposable article and the measurement peripheral 112 of the group 120 of components of the device, while the second critical interface 160 is located within the group 120, that is to say it is among the components of the device 100. The coding means 130, which is a component of the group 140, that is to say a component of the disposable article, must be very simple in this solution and in consequence has only a restricted information content. This is because the coding means 130 represents an element of the group 140 which characterizes the disposable article. Furthermore, the energy store 136, which is typically a battery, represents a further disposable article, which represents a separate consumable item and is not customer-friendly. The solution based on the device 100 and sketched in FIG. 1 admittedly offers the advantage that the generally expensive and therefore high-value, components are reused, this advantage does not, however, make up for the disadvantages that have been matched.

Figure 2:
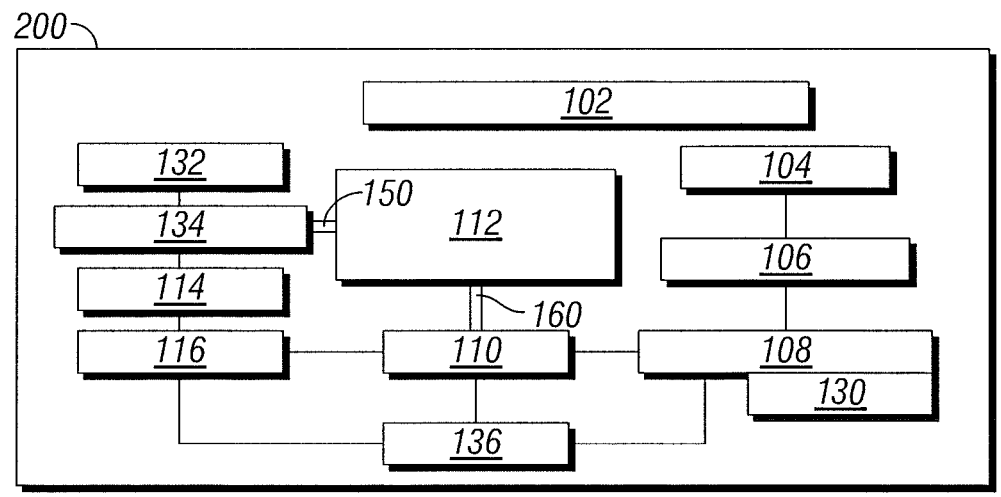
FIG. 2 illustrates a block diagram configuration of an analysis device which is generally in the form of a disposable system.

The illustration in FIG. 2 shows a further embodiment variant of an analysis system which is configured essentially in its entirety as a disposable system.

As can be seen from the illustration in FIG. 2, the device housing 102, the display 104 integrated in it, the display controller 106, the calculation electronics 108 and the coding means 130 which interacts with these electronics, the measurement electronics 110, and the measurement peripheral 112 are all connected to one another by means of the second critical interface 160, and the drive 114, the drive controller 116, the energy store 136 as well as the test strip magazine 134, which is connected to the measurement peripheral 112 via the first critical interface, together with the waste container 132, represent a generally disposable system 200. This disposable system 200 in FIG. 2 has the disadvantage that expensive components, such as the electronics and the display as well as the device housing, are also disposed of after a number of measurements, although it offers the advantage that it allows greater integration of the electronic components.

Figure 3:
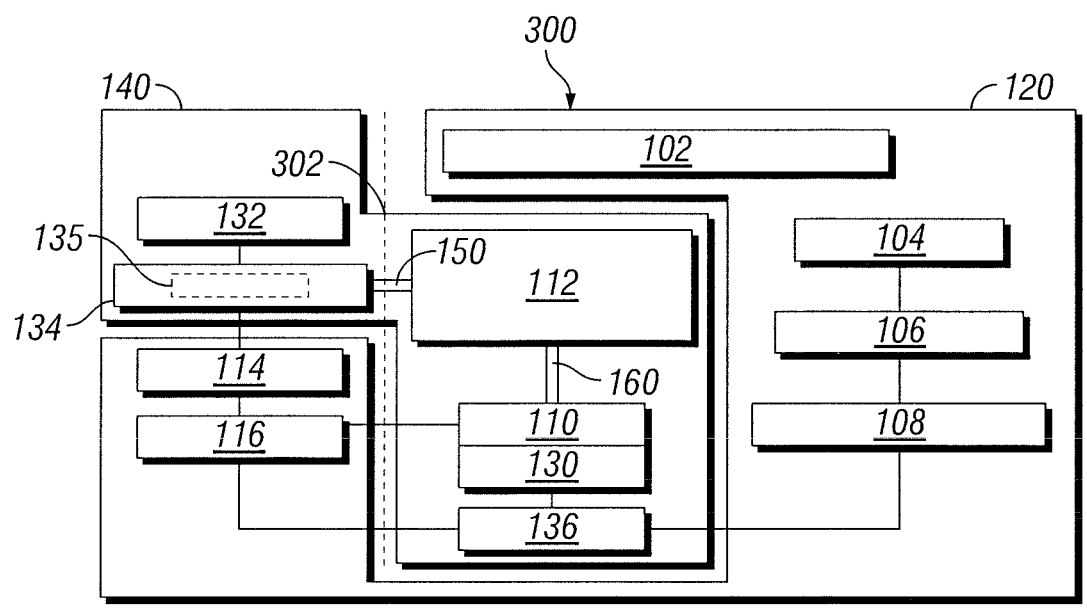
FIG. 3 illustrates a block diagram configuration of an embodiment of a measurement system proposed according to the present invention, with distributed functions, with the components of the analysis device being combined in one group and the components of an extended disposable article being combined in another, separate group, with the disposable group being formed from two parts which can be disconnected from one another.
Figure 4:
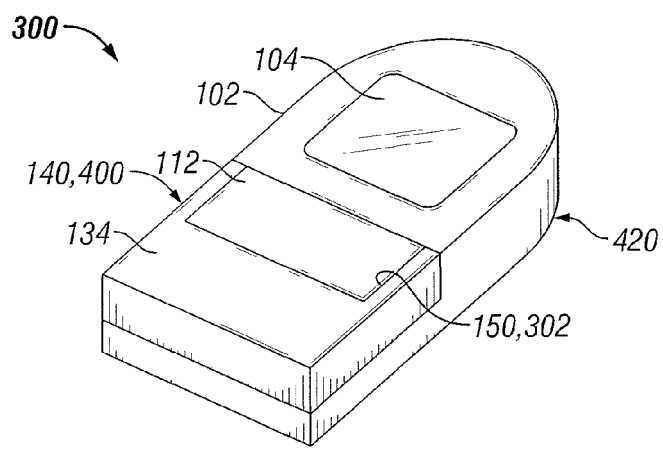
FIG. 4 is a perspective view of one embodiment of an analysis system.
Figure 5:
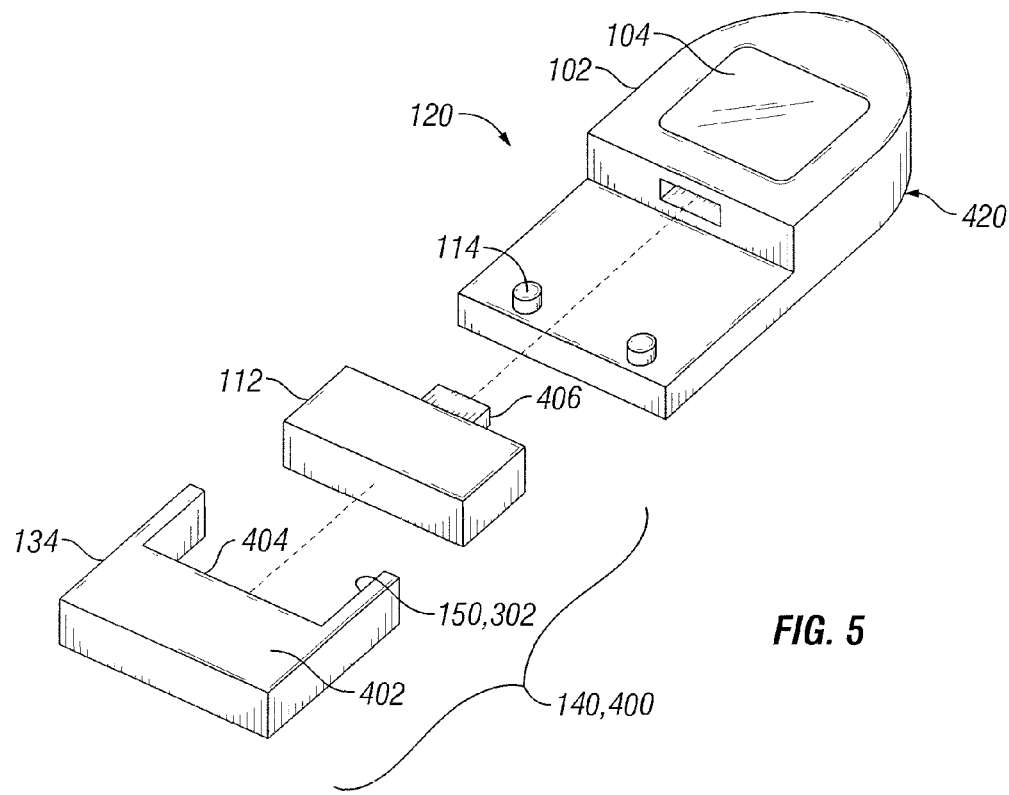
FIG. 5 is an exploded perspective view of the analysis system of FIG. 4.

FIG. 3 illustrates the integrated analysis system proposed according to the present invention with the functions arranged in a redistributed form, which will be compared in the following text with the known embodiments shown in FIGS. 1 and 2.

As can be seen from FIG. 3, the group 120 which comprises the elements of the analysis device comprises the device housing 102, the display 104, its display controller 106, the calculation electronics 108, as well as the drive 114 and its controller 116. This means that expensive device components, such as the drive 114, its controller 116 and the display 104 together with its controller 106 and the calculation electronics 108 are reused when the analysis system as illustrated in FIG. 3 and with distributed functions 300 is fitted with a new test strip magazine 134.

As can also be seen from the illustration in FIG. 3, the group 140 which contains the elements of the disposable article comprises the waste container 132, the already mentioned test strip magazine 134 and test elements 135 stored therein and, in this case, the measurement peripheral 112 and the measurement electronics 110 that are distinct from test elements 135, which are associated with a coding means 130, as well as an energy store 136. These components represent the elements of the group 140, which can be disposed of separately after use. This group 140, which is annotated with the reference symbol 140 in FIG. 3 and comprises the elements of the disposable article, includes the first critical interface 150 and the second critical interface 160. In the analysis system proposed according to the invention, the first critical interface 150 coincides with a disconnection point 302, at which the user connects the test strip magazine 134 together with the waste container 132 associated with it to the measurement peripheral 112. The disconnection point 302, which coincides with the first critical interface 150, advantageously allows the group 140 which represents the disposable article of the analysis system proposed according to the invention to be disconnected. The consumable materials without any electronics, for example the waste container 132 and the test magazine 134 can be disposed of in the domestic refuse while, a disconnection of the group 140 at the disconnection point 302, the electronic components, that is to say the measurement peripheral 112, the measurement electronics 110 connected to it via the second critical interface 160, together with coding means 130 associated with these electronics, in particular such as the battery storage device 136, to be recycled or at least to be supplied to an electronic strap disposal system, which was not possible in the case of the device 100 illustrated in FIGS. 1 and 2, or the disposable system 200 illustrated in FIG. 2.

As can also be seen from the solution proposed according to the invention that is illustrated schematically in FIG. 3, the first and the second critical interfaces 150, 160 are located in a component which is connected during production, that is to say the group 140. All the critical interfaces are joined and checked by the manufacturer. The functional reliability is improved, with less stringent requirements of mechanical tolerances, therefore reducing the production costs.

The configuration of the group 140 with the disconnection point 302 makes it possible for the user of the analysis system as illustrated in FIG. 3 to separately dispose of the electronic components 112, 110, 136 in the group 140 of the disposable article, or send them for recycling, without any problems. The separation between the waste container 132, which can be disposed of in the domestic reference, and the test strip magazine 134 without any test strips in it from the electronic components 110, 112, 130, 136 takes place at the interface 150, and this is extremely simple and convenient for the user.

As can also be seen from the schematic illustration in FIG. 3, the coding means 130 is directly associated with the measurement electronics 110. The direct association of the coding means 130 with the measurement electronics 110 has the advantage, to quote just one example, that this allows a higher level of integration, that is to say a smaller physical size of the device with an increase in the functionalities and a reduction in the costs, because of the lack of plug connections, which are susceptible to defects. Furthermore, it is possible to match the measurement electronics and measurement apparatus with a new disposable to the latest state of development, and to update the measurement electronics and measurement apparatus by means of a new disposable, so that the device 100 that is in use can be reused by the user. In this case, the disposable then represents the medium via which new information is passed to the device 100.

As can be seen from the illustration in FIG. 3, the group 140 of components of the disposable article includes the coding means 130. In comparison to the solutions according to the prior art, in which the coding means 130 contained only a limited amount of information, the coding means 130 which, according to the invention, is integrated in the group 140 of the disposable article, may be in the form of an ROM key or the like, for example, thus providing flexibility with regard to the information content. In the case of electronic storage media, the costs are generally split in a ratio of 1/3 for the storage chip, 1/3 for the housing and 1/3 for electrical contacts. The solution proposed according to the embodiments of the present invention makes it possible to save, for example, about 2/3 of these costs.

In an alternative embodiment of the group 140 illustrated in FIG. 3, which shows the components of the disposable article of the analysis system proposed according to the present invention with functions arranged in a distributed manner, it would also be feasible to disconnect the components comprising the waste container 132 as well as the empty and therefore used test strip magazine 134 from the electronic components 112, 110 and 136 along the disconnection point 302, and to fit a new test strip magazine 134, fitted with a fresh unconsumed supply, together with a waste container 132 to the electronic components 112, 110, 136 which may still be intact, and once again use a reusable group 140 such as this within the system 300 with functions arranged in a distributed manner.

The system 300 illustrated in FIG. 3 with functions arranged in a distributed manner allows reuse of expensive components such as the drive 114, the motor controller 116 associated with it, the display 104, the display controller 106, the calculation electronics 108 and the device housing 102.

The features disclosed in the above description, the claims and the drawings may be important both individually and in any combination with one another for implementing the invention in its various embodiments.

It is noted that terms like "preferably", "commonly", and "typically" are not utilized herein to limit the scope of the claimed invention or to imply that certain features are critical, essential, or even important to the structure or function of the claimed invention. Rather, these terms are merely intended to highlight alternative or additional features that may or may not be utilized in a particular embodiment of the present invention.

For the purposes of describing and defining the present invention it is noted that the term "substantially" is utilized herein to represent the inherent degree of uncertainty that may be attributed to any quantitative comparison, value, measurement, or other representation. The term "substantially" is also utilized herein to represent the degree by which a quantitative representation may vary from a stated reference without resulting in a change in the basic function of the subject matter at issue.

Having described the present invention in detail and by reference to specific embodiments thereof, it will be apparent that modification and variations are possible without departing from the scope of the present invention defined in the appended claims. More specifically, although some aspects of the present invention are identified herein as preferred or particularly advantageous, it is contemplated that the present invention is not necessarily limited to these preferred aspects of the present invention.

What is claimed is:

1. An integrated analysis system for determining an analyte in a body fluid, the system comprising:
    an analysis device including a device housing, a display, a display controller connected to the display operable to control the display, and calculation electronics connected to the display controller operable to calculate data displayed on the display;
    a measurement unit for storing and evaluating test elements, the measurement unit including:
        a magazine with a housing storing a plurality of test elements;
        a measurement peripheral with measurement electronics configured to evaluate one or more test elements in the measurement unit that are wetted with the body fluid and an interface connected to the measurement electronics, the measurement peripheral being removably fitted to the housing of the magazine with the interface positioned relative to the magazine in order to facilitate connection with the analysis device; and
        wherein the interface is configured to removably mechanically couple the magazine to the analysis device.

2. The analysis system according to claim 1, wherein the measurement peripheral includes at least one coding means integrated with the measurement electronics.

3. The analysis system according to claim 2, wherein the at least one coding means comprises an electronic memory chip.

4. The analysis system according to claim 1, wherein the measurement unit further comprises at least one energy store, wherein during production of the analysis system at least one critical interface is provided and tested between one or more pairings selected from the group consisting of the test element magazine and the measurement peripheral, the measurement peripheral and the measurement electronics, and the measurement electronics and the at least one energy store.

5. The analysis system according to claim 1, wherein the measurement electronics and the measurement peripheral can be fitted with a new, unused, magazine of test elements.

6. The analysis system according to claim 1, wherein the measurement peripheral comprises an optical evaluation system for optical evaluation of test elements which are stored in the magazine.

7. The analysis system according to claim 1, wherein the measurement peripheral comprises an electrochemical evaluation system for electrochemical evaluation of test elements which are stored in the magazine.

8. The analysis system according to claim 1, wherein the fitting of the test element magazine and the measurement peripheral is connected during production of the analysis system.

9. The analysis system according to claim 1, wherein the analysis system comprises at least one energy store included in the measurement unit.

10. The analysis system according to claim 1, wherein the analysis system comprises at least one energy store included in the analysis device.

11. The analysis system according to claim 1, wherein the measurement peripheral includes at least one circuit board including a serial interface, wherein the analysis device is configured to be plugged on to the serial interface to receive data relating a glucose measurement.

12. The analysis system according to claim 1, wherein the measurement peripheral includes at least one moisture sensor configured to measure a moisture content in a chamber of the magazine and at least one processor configured to determine at least one of a quality and a useful life of the test elements stored in the magazine based on the moisture content.

13. The analysis system according to claim 1, wherein the measurement unit includes an energy store that is detachably connected to the magazine, wherein the connection of the magazine to the measurement peripheral makes an electrical connection between the energy store and the measurement electronics.

14. The analysis system according to claim 1, wherein the measurement peripheral is operable to evaluate a selected test element from the magazine for at least one analyte in the body fluid sample applied to the test element.

15. The analysis system according to claim 1, wherein the measurement electronics include a circuit board and the interface is a serial interface connected to the circuit board configured to transmit signals from the measurement electronics to the calculation electronics of the analysis device.

16. The analysis system according to claim 1, wherein the analysis device is configured to be plugged onto the interface of the measurement unit.

17. The analysis system according to claim 1, wherein the analysis device includes a drive for driving test elements from the magazine.

* * * * *